United States Patent [19]

Jakobovits

[11] Patent Number: 5,714,352
[45] Date of Patent: Feb. 3, 1998

[54] DIRECTED SWITCH-MEDIATED DNA RECOMBINATION

[75] Inventor: Aya Jakobovits, Menlo Park, Calif.

[73] Assignee: Xenotech Incorporated, Foster City, Calif.

[21] Appl. No.: 619,109

[22] Filed: Mar. 20, 1996

[51] Int. Cl.$^6$ .......................... C12N 15/63; C12N 15/79; C12N 5/08; C12N 5/24
[52] U.S. Cl. ................... 435/172.3; 435/320.1; 435/328; 435/372.3
[58] Field of Search ............... 435/69.1, 70.21, 435/172.3, 320.1, 325, 326, 328, 372.3; 536/23.1, 23.53

[56] References Cited

U.S. PATENT DOCUMENTS

| 4,816,567 | 3/1989 | Cabilly et al. | 530/387.3 |
| 5,202,238 | 4/1993 | Fell et al. | 435/69.6 |

FOREIGN PATENT DOCUMENTS

WO 86/01533   3/1986   WIPO.

OTHER PUBLICATIONS

Leung et al. (1994) Mol. Cell Biol. 14:1450–1458, 1994.
Harriman et al. (1993) Annu. Rev. Immunol. 11:361–384, 1993.
Dariavach, P. et al. *The Mouse IgH 3'-enchancer, Eur. J. Immunol.*, 21:1499–1504, (1991).
Flanagan, J.G. et al., *Arrangement of human immunoglobulin heavy chain constant region genes implies evolutionary duplication of a segment containing γ, ε and α genes, Nature,* vol. 300, 23/30, pp. 709–713, (Dec. 1982).
Green, L.L., et al., *Antigen–specific human monoclonal antibodies from mice engineered with human Ig heavy and light chain YACs, Nature Genetics,* vol. 7, pp. 13–21, (May 1994).
Gritzmacher, C., *Molecular Aspects of Heavy–chain Class Switching, Critical Reviews in Immunology,* vol. 9, Issue 3, pp. 173–200, (1989).
Honjo, T., *Immunoglobulin Genes, Ann. Rev. Immunol.,* 1:499–528, (1983).
Marcu, K. B., et al., *A model for the molecular requirements of immunoglobulin heavy chain class switching, Nature,* vol. 298, 87–89, (Jul. 1, 1982).
Mills, Frederick, C., et al., *Human Ig Sγ Regions and Their Participation in Sequential Switching to IgE, J. Immunol.,* 155:3021–3036, (1995).
Mowatt, M. R., et al., *DNA Sequence of the Murine γ1 Switch Segment Reveals Novel Structural Elements, Journal of Immunology,* vol. 136, No. 7, 2674–2683, (Apr. 1, 1986).
Nikaido, T., et al., *Nucleotide Sequences of Switch Regions of Immunoglobulin $C_e$, and $C_γ$Genes and Their Comparison, the Journal of Biological Chemistry,* vol. 257, 13:7322–7329, (Jul. 10, 1982).
Rabbits, T.H., et al., *The role of gene deletion in the immunoglobulin heavy chain switch, Nature,* vol. 283:351–356, (Jan. 24, 1980).
Shimizu, A., et al., *Trans–Splicing as a Possible Molecular Mechanism for the Multiple Isotype Expression of the Immunoglobulin Gene, J. Exp. Med.,* 173:1385–1393, (Jun. 1991).
Takahashi, N., et al., *Structure of Human Immunoglobulin Gamma Genes: Implications for Evolution of a Gene Family, Cell,* 29:671–679, (Jun. 1982).

*Primary Examiner*—George G. Elliott
*Assistant Examiner*—Robert Schwartzman
*Attorney, Agent, or Firm*—Karl Bozicevic; Fish & Richardson P.C.

[57] ABSTRACT

Switch regions derived from an immunoglobulin (Ig) gene are used to direct recombination between a targeting construct containing a promoter, a switch region ($S_1$), and 2) a target locus minimally containing a promoter, a switch region ($S_2$), and a target sequence.

25 Claims, 6 Drawing Sheets

Directed S-S Recombination with Target Locus

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
  ( A ) LENGTH: 45 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:1:

GCATGCCCGC GGGAATAGGC GGGCTTTTTT NNNGCCGCGG CTCGA        45

DIRECTED SWITCH-MEDIATED DNA RECOMBINATION

FIELD OF THE INVENTION

This invention relates generally to methods and compositions for use in recombinant DNA technology, particularly in methods for manipulation of DNA sequences encoding antibodies, proteins, or portions thereof.

BACKGROUND OF THE INVENTION

The basic immunoglobulin (Ig) structural unit in vertebrate systems is composed of two identical "light" polypeptide chains (approximately 23 kDa), and two identical "heavy" chains (approximately 53 to 70 kDa). The four chains are joined by disulfide bonds in a "Y" configuration, and the "tail" portions of the two heavy chains are bound by covalent disulfide linkages when the immunoglobulins are generated either by B cell hybridomas or other cell types.

A schematic of the general antibody structure is shown in FIG. 1. The light and heavy chains are each composed of a variable region at the N-terminal end, and a constant region at the C-terminal end. In the light chain, the variable region (termed "$V_L J_L$") is composed of a variable ($V_L$) region connected through the joining ($J_L$) region to the constant region ($C_L$). In the heavy chain, the variable region ($V_H D_H J_H$) is composed of a variable ($V_H$) region linked through a combination of the diversity ($D_H$) region and the joining ($J_H$) region to the constant region ($C_H$). The $V_L J_L$ and $V_H D_H J_H$ regions of the light and heavy chains, respectively, are associated at the tips of the Y to form the antibody's antigen binding portion and determine antigen binding specificity.

The ($C_H$) region defines the antibody's isotype, i.e., its class or subclass. Antibodies of different isotypes differ significantly in their effector functions, such as the ability to activate complement, bind to specific receptors (e.g., Fc receptors) present on a wide variety of cell types, cross mucosal and placental barriers, and form polymers of the basic four-chain IgG molecule.

Antibodies are categorized into "classes" according to the $C_H$ type utilized in the immunoglobulin molecule (IgM, IgG, IgD, IgE, or IgA). There are at least five types of $C_H$ genes (Cμ, Cγ, Cδ, Cε, and Cα), and some species (including humans) have multiple $C_H$ subtypes (e.g., $C\gamma_1$, $C\gamma_2$, $C\gamma_3$, and $C\gamma_4$ in humans). There are a total of nine $C_H$ genes in the haploid genome of humans, eight in mouse and rat, and several fewer in many other species. In contrast, there are normally only two types of light chain constant regions ($C_L$), kappa (κ) and lambda (λ), and only one of these constant regions is present in a single light chain protein (i.e., there is only one possible light chain constant region for every $V_L J_L$ produced). Each heavy chain class can be associated with either of the light chain classes (e.g., a $C_H\gamma$ region can be present in the same antibody as either a κ or λ light chain), although the constant regions of the heavy and light chains within a particular class do not vary with antigen specificity (e.g., an IgG antibody always has a Cγ heavy chain constant region regardless of the antibody's antigen specificity).

Each of the V, D, J, and C regions of the heavy and light chains are encoded by distinct genomic sequences. Antibody diversity is generated by recombination between the different $V_H$, $D_H$, and $J_H$ gene segments in the heavy chain, and $V_L$ and $J_L$ gene segments in the light chain. The recombination of the different $V_H$, $D_H$, and $J_H$ genes is accomplished by DNA recombination during B cell differentiation. Briefly, the heavy chain sequence recombines first to generate a $D_H J_H$ complex, and then a second recombinatorial event produces a $V_H D_H J_H$ complex. A functional heavy chain is produced upon transcription followed by splicing of the RNA transcript. Production of a functional heavy chain triggers recombination in the light chain sequences to produce a rearranged $V_L J_L$ region which in turn forms a functional $V_L J_L C_L$ region, i.e., the functional light chain.

During the course of B cell differentiation, progeny of a single B cell can switch the expressed immunoglobulin isotype from IgM to IgG or other classes of immunoglobulin without changing the antigen specificity determined by the variable region. This phenomenon, known as immunoglobulin class-switching, is accompanied by DNA rearrangement that takes place between switch (S) regions located 5' to each $C_H$ gene (except for Cγ) (reviewed in Honjo (1983) Annu. Rev. Immunol. 1:499–528, and Shimizu & Honjo (1984) Cell 36:801–803). S—S recombination brings the $V_H D_H J_H$ exon to the proximity of the $C_H$ gene to be expressed by deletion of intervening $C_H$ genes located on the same chromosome. The class-switching mechanism is directed by cytokines (Mills et al. (1995) J. Immunol. 155:3021–3036). Switch regions vary in size from 1 kb (Sε) to 10 kb ($S\gamma_1$), and are composed of tandem repeats that vary both in length and sequence (Gritzmacher (1989) Crit. Rev. Immunol. 9:173–200). Several switch regions have been characterized including the murine Sμ, Sε, Sγ, Sγ3, Sγ1, Sγ2b and Sγ2a switch regions and the human Sμ switch region (Mills et al. (1995) Supra; Nikaido et al. (1981) Nature 292:845–8; Marcu et al. (1982) Nature 298:87–89; Takahashi et al. (1982) Cell 29:671–9; Mills et al. (1990) Nucleic Acids Res. 18:7305–16; Nikaido et al. (1982) J. Biol. Chem. 257:7322–29; Stanton et al. (1982) Nucleic Acids Res. 10:5993–6006; Gritzmacher (1989) supra; Davis et al. (1980) Science 209:1360; Obata et al. (1981) Proc. Natl. Acad. Sci. U.S.A. 78:2437–41; Kataoka et al. (1981) Cell 23:357; Mowatt et al. (1986) J. Immunol. 136:2674–83; Szurek et al. (1985) J. Immunol. 135:62014 6; and Wu et al. (1984) EMBO J. 3:2033–40).

Observations that a single B cell can express more than one isotype simultaneously on its surface is not explained by the class-switching mechanism since S—S recombination is limited to intrachromosomal recombination and results in deletion of the exchanged $C_H$ gene. A second mechanism, called trans-splicing, has been described in which two transcripts generated from different chromosomes are joined to form a single continuous transcript (Shimizu et al. (1991) J. Exp. Med. 173:1385–1393). Transgenic mice carrying a rearranged expressible $V_H D_H J_H$ heavy chain μ gene integrated outside the mouse IgH locus were found to produce mRNA having the $V_H D_H J_H$ region of the transgene correctly spliced to the endogenous C. region. As with S—S recombination, the frequency of trans-splicing is low, and the factors regulating both mechanisms are not well understood.

The value and potential of antibodies as diagnostic and therapeutic reagents has been long-recognized in the art. Unfortunately, the field has been hampered by the slow, tedious processes required to produce large quantities of an antibody of a desired specificity. The classical cell fusion techniques allowed for efficient production of monoclonal antibodies by fusing the B cell producing the antibody with an immortalized cell line. The resulting cell line is called a hybridoma cell line. However, most of these monoclonal antibodies are produced in murine systems and are recognized as "foreign" proteins by the human immune system. Thus the patient's immune system elicits a response against the antibodies, which results in antibody neutralization and clearance, and/or potentially serious side-effects associated with the anti-antibody immune response.

One approach to this problem has been to develop human or "humanized" monoclonal antibodies, which are not as easily "recognized" as foreign epitopes, and avoid an anti-antibody immune response in the patient. Applications of human B cell hybridoma-produced monoclonal antibodies have promising potential in the treatment of cancer, microbial, and viral infections, B cell immunodeficiencies associated with abnormally low antibody production, autoimmune diseases, inflammation, transplant rejection and other disorders of the immune system, and other diseases. However, several obstacles remain in the development of such human monoclonal antibodies. For example, many human tumor antigens may not be immunogenic in humans and thus it may be difficult to isolate human B cells producing antibodies against human antigens.

Attempts to address the problems associated with antibodies for human therapeutics have used recombinant DNA techniques. Most of these efforts have focused on the production of chimeric antibodies having a human $C_H$ region and non-human (e.g., murine) antigen combining (variable) regions. These chimeric antibodies are generally produced by cloning the desired antibody variable region and/or constant region, combining the cloned sequences into a single construct encoding all or a portion of a functional chimeric antibody having the desired variable and constant regions, introducing the construct into a cell capable of expressing antibodies, and selecting cells that stably express the chimeric antibody. Alternatively, the chimeric antibody is produced by cloning the desired variable region or constant region, introducing the construct into an antibody-producing cell, and selecting for chimeric antibody-producing cells that result from homologous recombination between the desired variable region and the endogenous variable region, or the desired constant region and the endogenous constant region. Examples of techniques which rely upon recombinant DNA techniques such as those described above to produce chimeric antibodies are described in PCT Publication No. WO 86/01533 (Neuberger et al.), and in U.S. Pat. Nos. 4,816,567 (Cabilly et al.) and 5,202,238 (Fell et al.). These methods require transferring DNA from one cell to another, thus removing it from its natural locus, and thus require careful in vitro manipulation of the DNA to ensure that the final antibody-encoding construct is functional (e.g., is capable of transcription and translation of the desired gene product).

There is a clear need in the field for a method for producing a desired protein or antibody which does not require multiple cloning steps, in more efficient than conventional homologous recombination, and can be carried out in hybridoma cells.

SUMMARY OF THE INVENTION

The present invention features a method of replacing one DNA sequence with another using switch (S) regions derived from an immunoglobulin (Ig) gene. The method of the invention allows any two pieces of DNA to be "switched" or a piece of exogenous DNA to be inserted into a site containing a natural or artificial S region. Thus the method of the invention allows directed recombination to occur and eliminates many cloning steps required by current recombinant DNA methods.

In the method of the invention, directed recombination is brought about between a targeting construct and a target locus. The nucleic acid targeting construct is composed minimally of a switch region and a promoter operably linked to and 5' of the switch region. Additionally, depending on the desired recombinatorial product, the targeting construct can also contain a modifying sequence operably linked to and 3' of the switch region, and other DNA sequences between the promoter and switch regions, e.g., 5' of the switch region and 3' of the promoter region. Of particular interest is the use of a targeting construct with an Ig heavy chain to facilitate isotype switching, e.g., replacement of an endogenous constant region ($C_H$) in an antibody heavy chain gene (target sequence) with a $C_H$ of a different subtype, isotype, or species of origin (modifying sequence). For example, exogenous DNA encoding the constant or variable region of an antibody light or heavy chain can be switched with the constant or variable region of an endogenous sequence to create a sequence which encodes an antibody with a different constant or variable region. In a broader sense, the method of the invention is widely applicable to manipulate DNA sequences for production of a desired protein or protein component, including the production of chimeric antibodies having a desired variable region linked to a non-antibody polypeptide (e.g., a detectable polypeptide label, or a polypeptide having a desired activity).

In one aspect, the invention features a method for directed switch-mediated recombination by a) introducing a targeting construct into a cell having a target locus, the target locus being minimally composed of a promoter, a switch region, and a target sequence, wherein the targeting construct is minimally composed of a promoter and a switch region, and can contain additional modifying sequences, b) culturing the cell to allow transcription of the target locus and the targeting construct, thereby promoting recombination of the switch regions of the target locus and the targeting construct, and c) selecting a cell containing the desired recombined DNA product sequence, minimally composed of a switch region (composed of DNA sequences from one or both the target locus switch region and targeting construct switch region).

In a specific embodiment of the invention, the targeting construct ($P_1$-$S_1$) is composed of a promoter ($P_1$) and switch region ($S_1$) and the target locus ($P_2$-$S_2$-T) is composed of a promoter ($P_2$), a naturally occurring or artificially inserted switch region ($S_2$), and a target sequence (T). Directed S—S recombination between the S—S regions results in a DNA sequence having the $P_1$ promoter of the targeting construct, a switch region containing DNA sequences from one or both $S_1$ and $S_2$ regions, and the T sequence ($P_1$-$S_1$/$S_2$-T). In this embodiment, the target sequence is removed from the control of the target locus promoter and placed under control of the desired $P_1$ promoter. Cells containing the desired DNA sequence are selected by methods known in the art, including Southern blot analysis or PCR.

In another embodiment, the targeting construct ($P_1$-$S_1$-M) is composed of a promoter ($P_1$), a switch region ($S_1$), and a modifying sequence (M), and the target locus ($P_2$-$S_2$-T) is composed of a promoter ($P_2$), a naturally occurring or artificially inserted switch region ($S_2$), and a target sequence (T). Directed S—S recombination between the S—S regions results in two possible recombinatorial product sequences, one having the $P_1$ promoter of the targeting construct, a switch region containing DNA sequences from one or both $S_1$ and $S_2$ regions, and the T sequence ($P_1$-$S_1$/$S_2$-T), and a second sequence having a $P_1$ promoter, a switch region containing DNA sequences from one or both $S_1$ and $S_2$ regions, and the M sequence ($P_1$-$S_1$/$S_2$-M). In this embodiment, cells expressing the M sequence are selected by methods known in the art, including Southern or Northern blot analysis.

In a third embodiment, the targeting construct ($P_1$-Z-$S_1$) is composed of a promoter ($P_1$), DNA sequences 5' to the switch region (Z), and the switch region ($S_1$). The target locus ($P_2$-$S_2$-T) is composed of a promoter ($P_2$), a naturally occurring or artificially inserted switch region ($S_2$), and a target sequence (T). Directed S—S recombination between the switch regions results in a DNA sequence having the $P_1$ promoter of the targeting construct, the Z DNA sequences, a switch region containing DNA sequences from one or both switch regions, and the T sequence ($P_1$-Z-$S_1$/$S_2$-T).

The target locus is a DNA sequence having a switch region, and may be a native, naturally-occurring sequence (e.g., an Ig locus of an antibody-producing cell), a rearranged Ig locus, or a recombinantly produced DNA sequence artificially inserted at a desired site. The target locus can be either an extrachromosomal element or a stably integrated chromosomal element. Preferably, the target locus encodes an antibody heavy chain gene. The targeting construct is either an extrachromosomal element or a stably integrated chromosomal element. Where the target locus is an antibody heavy chain gene, the modifying sequence of the targeting construct preferably encodes a different or modified heavy chain constant region or a non-antibody sequence of interest (e.g., a detectable polypeptide label, an enzyme, a toxin, or a growth factor).

The invention provides a method of modifying a DNA sequence by directed S—S recombination. The invention allows DNA recombination to be directed to any site which contains a naturally-occurring switch region or synthetic switch region, including a site into which an S region has been artificially inserted.

The invention provides a method to replace or modify a first DNA sequence (a target sequence) with a second DNA sequence (a modifying sequence) without the need for isolating the nucleotide sequence containing the target sequence, excising the target sequence, and ligating the modifying sequence in place of the target sequence. The invention also provides a method to replace portions of a polypeptide-encoding sequences with a heterologous amino acid sequence, where the polypeptide is composed of two distinct components (e.g., an N-terminal component and a C-terminal component) that, for example, confer distinct functional or structural characteristics upon the polypeptide (e.g., ligand binding or cell-binding). For example, the invention allows for the substitution of either the N-terminal portion with a different, heterologous amino acid-encoding sequence, or the C-terminal portion with a different, heterologous amino acid-encoding sequence.

Directed switch-mediated recombination allows recombination to occur at a specific, pre-selected region with an increased efficiency relative to the naturally-occurring mechanism which is limited to the immunoglobulin heavy chain. The method of the invention removes switch-mediated recombination from the limitations of its normal regulatory environment, allowing recombination to be controlled as needed with, for example, the use of constitutive or inducible promoters.

The ability to accomplish directed in vitro S-mediated recombination avoids tedious, time-consuming manipulation of DNA using conventional recombinant DNA techniques while providing a highly efficient method of inserting a DNA sequence. For example, the method allows the detectable label portion of fusion proteins (e.g., α-galactosidase) to be readily exchanged for a different amino acid sequence (e.g., alkaline phosphatase).

In a specific application of the method of the invention, directed S—S recombination is used to replace the constant region of an antibody heavy chain gene with a different or modified constant region without the need for extensive manipulation of the antibody heavy chain gene. Additionally, the method of the invention allows the antibody gene to be maintained in its native locus.

These and other objects, advantages and features of the present invention will become apparent to those persons skilled in the art upon reading the details of the compositions, composition components, methods and method steps of the invention as set forth below.

DETAILED DESCRIPTION

Figure 1:
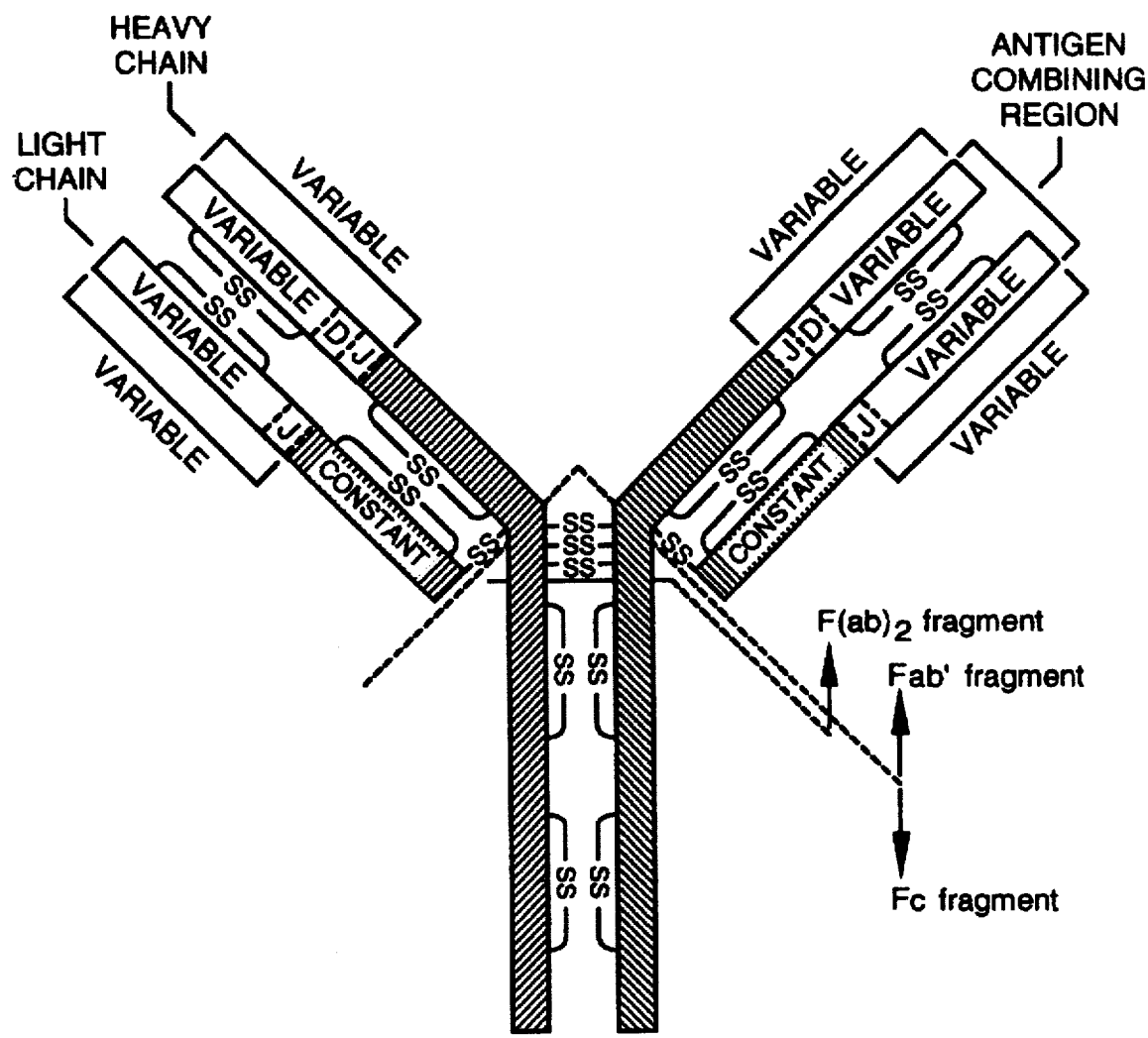
FIG. 1 is a schematic showing the basic immunoglobulin structure.

Before the methods and compositions of the present invention are described and disclosed it is to be understood that this invention is not limited to the particular methods and compositions described as such may, of course, vary. It is also to be understood that the terminology used herein is for the purpose of describing particular embodiments only, and is not intended to be limiting since the scope of the present invention will be limited only by the appended claims.

It must be noted that as used in this specification and the appended claims, the singular forms "a", "an" and "the" include plural referents unless the context clearly dictates otherwise. Thus, for example, reference to "a DNA sequence" includes a plurality of DNA sequences and different types of DNA sequences.

Unless defined otherwise all technical and scientific terms used herein have the same meaning as commonly understood by one of ordinary skill in the art to which this invention belongs. Although any materials or methods similar or equivalent to those described herein can be used in the practice or testing of the present invention, the preferred methods and materials are now described. All publications mentioned herein are incorporated herein by reference for the purpose of describing and disclosing the particular information for which the publication was cited in connection with. The publications discussed above are provided solely for their disclosure prior to the filing date of the present application. Nothing herein is to be construed as an admission that the inventor is not entitled to antedate such disclosure by virtue of prior invention.

Definitions

The term "artificial" as used with "artificial construct" or "artificial switch region" and the like, refers to an isolated natural or non-naturally occurring material e.g., a nucleotide sequence manufactured by human intervention e.g., fusing natural sequences together or chemically synthesizing natural sequences in isolation.

The term "switch region" means a nucleotide sequence composed of tandem repeat sequences that occur in nature 5' to the immunoglobulin heavy chain constant region and function in intrachromosomal class-switching, i.e., recombination of DNA sequences encoding specific portions of immunoglobulin heavy chain constant regions. Examples of specific switch region sequences are disclosed in Mills et al. (1995) J. Immunol. 155:3021–3036, herein specifically incorporated by reference. "Switch region" includes both full-length switch sequences of native immunoglobulin sequences, as well as recombinant and synthetic nucleotide sequences that are modified (e.g., contain nucleotide substitutions, additions, mutations, and/or other modifications) relative to a native immunoglobulin switch region, with the proviso that the switch region retains its function in facilitating recombination when transcribed.

The term "switch-mediated recombination" or "directed S—S recombination" are used interchangeably to mean interchromosomal, intrachromosomal, or extrachromosomal DNA recombination facilitated by a switch region. For example, S—S recombination results from interaction of 1) a first switch region positioned 3' to a promoter (targeting construct) and 2) a second switch region positioned 3' to a promoter and 5' to a DNA sequence (target locus). Following activation of transcription of the first and second switch regions, recombination occurs between the switch regions resulting in an alteration of the target locus DNA sequence. The directed S—S recombination of the invention results in interaction between DNA sequences on two different chromosomes, on the same chromosome, between a chromosome and an extrachromosomal element, or between two extrachromosomal elements.

The term "targeting construct" means a nucleic acid construct which is introduced into a cell to cause directed S—S recombination at a natural or artificial switch region. A targeting construct minimally comprises: 1) a switch region and 2) a promoter operably linked to and 5' of the switch region. Optionally, the targeting construct further comprises 3) a modifying sequence operably linked to and 3' of the switch region. The targeting construct may also comprise 4) one or more DNA sequences between the switch region and promoter. Depending on the actual targeting construct used, the resulting mRNA will encode the switch region, or the switch region and the modifying sequence, or the switch region and DNA sequences between the switch region and/or a modifying sequence.

The term "target locus" means a nucleic acid sequence minimally comprises 1) a switch region, 2) a target sequence adjacent and 3' of the switch region, and 3) a promoter operably positioned in the target locus to provide transcription of the switch region and target sequence as one or more translatable mRNA(s). The target locus can further contain an additional DNA sequence positioned adjacent and 5' of the switch region; in such constructs, the promoter provides transcription of the additional DNA sequence, the switch region, and the target sequence as one or more translatable mRNA(s). "Target loci" can be either naturally occurring (e.g., an immunoglobulin gene composed of a rearranged VDJ region positioned 5' of a switch region and $C_H$ gene) or recombinantly or synthetically produced, and can be either chromosomal or extrachromosomally located. An exemplary target sequence comprises a promoter sequence operatively positioned 5' to a switch region operatively positioned 5' to a coding sequence which is preferably a sequence encoding a constant region of a human antibody.

The terms "target sequence" means the nucleic acid sequence adjacent to a switch region where directed S—S recombination takes place. In one embodiment of the method of the invention, a target sequence is replaced by the modifying sequence after switch-mediated recombination. "Target sequences" can be naturally occurring sequences endogenous to a chromosomal sequence or recombinant sequences (i.e., a sequence produced using recombinant genetic manipulation) present as an extrachromosomal element (e.g., a vector) or as a stably integrated element within a chromosomal sequence. Target sequences are adjacent to a switch region which may be a naturally occurring switch region or may be a switch region inserted 5' to a desired target sequence by recombinant DNA technology. Exemplary target sequences are different from the modifying sequence and include sequences encoding an immunoglobulin heavy chain constant region of a particular isotype, subtype, and/or origin.

The term "immunoglobulin (Ig) loads" means a nucleotide sequence that encodes all or a portion of the constant region and/or variable region of an antibody molecule, including all or portions of the regulatory sequences that control expression of an antibody molecule from the locus or its processes. Heavy chain genes in Ig loci include but are not limited to all or a portion of the $V_H$, $D_H$, $J_H$, and constant regions, as well as the switch regions, intronic sequences, and flanking sequences associated with or adjacent the heavy chain gene. Ig loci for light chains include but are not limited to the $V_L$, $J_L$, and constant regions of both the kappa and lambda alleles, intronic sequences, and flanking sequences associated with or adjacent the light chain gene.

The term "modified target locus" means a nucleic acid sequence modified by switch-mediated DNA recombination so that the modified target sequence is minimally composed of a switch region composed of switch sequences derived from the unmodified target locus switch region, or from both the unmodified target locus and the targeting construct. In one embodiment of the invention, the modified target locus is also composed of the promoter of the unmodified target sequence, the first DNA sequence of the unmodified target sequence (when present in the original target locus), and the modifying sequence of the targeting construct. Activation of transcription by the promoter results in transcription of the first DNA sequence, the switch region, and the modifying sequence in one or more translatable mRNA(s).

The term "promoter" means a nucleotide sequence that, when operably linked to a DNA sequence of interest, promotes transcription of that DNA sequence.

The term "detectable polypeptide label" means a amine acid sequence that, when covalently bound to another amine acid sequence, provides a heterologous sequence that can be readily detected. For example, the polypeptide can be detected by binding of a polypeptide-specific antibody, by virtue of an enzymatic activity of the polypeptide, or by reaction of the polypeptide with a chemical reagent. Exemplary detectable polypeptide labels include β-galactosidase, alkaline phosphatase, horseradish peroxidase, enzymatically active portions of these enzymes, or any amino acid sequence that is immunodetectable and heterologous to the amino acid sequence with which it is associated.

Directed S—S Recombination (General)

The method of directed switch region-mediated recombination uses switch regions (e.g., those isolated and derived from an immunoglobulin locus) to facilitate recombination at a specific nucleic acid sequence. The nucleic acid sequence to which S—S recombination is directed contains an S region and is termed a "target locus," while the introduced nucleic acid sequence containing a S region sequence is termed a "targeting construct." Transcription of each S region allows S—S recombination to occur between the two preselected DNA regions. The presence of a selected promoter provides constitutive or inducible transcription, thereby enhancing the frequency of S—S recombination occurrence.

Figure 2A:
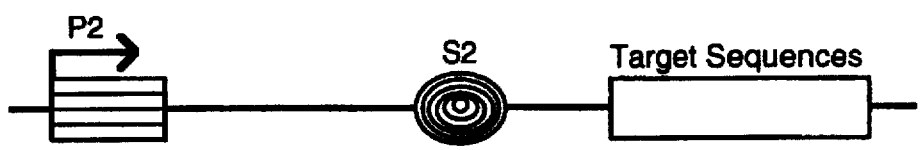
FIG. 2A is a schematic showing the basic components of a target locus consisting of a promoter ($P_2$), switch region ($S_2$), and a target sequence (T).
Figure 2B:
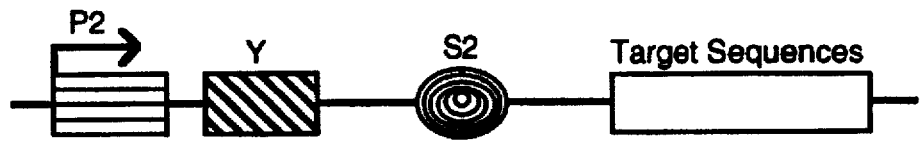
FIG. 2B is a schematic showing the basic components of a target locus consisting of a promoter ($P_2$), DNA sequences positioned 3' of the promoter and 5' of the switch region (Y), switch region ($S_2$), and a target sequence (T).

The basic components of an exemplary target locus suitable for use in the invention are illustrated in FIG. 2A. The minimal components of the target locus are (from 5' to 3'): 1) a promoter ($P_2$, where the arrow indicates the direction of transcription), 2) a switch region ($S_2$), and 3) a target sequence (T). Alternatively, the target locus can further contain an additional DNA sequence positioned 3' of the promoter and 5' of the switch region (Y) (FIG. 2B). Regardless of its composition, the target locus components are positioned so that the promoter activates transcription of the 5' DNA sequence (optional), switch region, and target sequence (optional). The target locus can either be an endogenous, naturally-occurring chromosomal sequence (e.g., an Ig heavy chain locus where the 5' DNA sequence is a $V_H D_H J_H$ gene and the target sequence is a $C_H$ gene) or an artificially constructed sequence (i.e., a recombinantly produced sequence or a synthesized sequence) which is present as either an extrachromosomal element (e.g., a vector or plasmid) or as a stable chromosomal integrant.

Figure 3A:
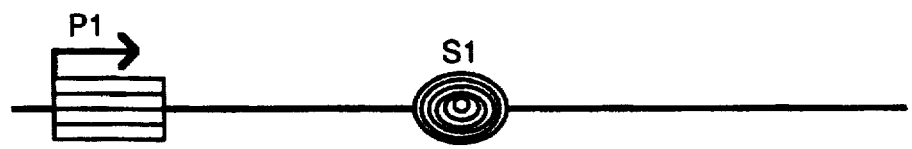
FIG. 3A is a schematic showing the basic components of a targeting construct consisting of a promoter ($P_1$) and switch region ($S_1$).
Figure 3B:
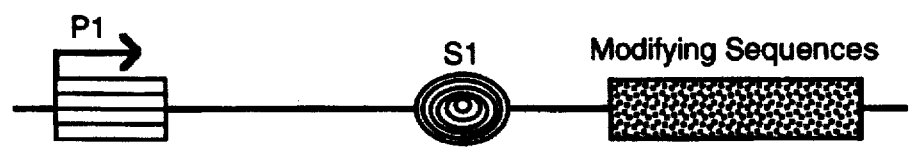
FIG. 3B is a schematic showing the basic components of a targeting construct consisting of a promoter ($P_1$), switch region ($S_1$), and modifying sequences.
Figure 3C:
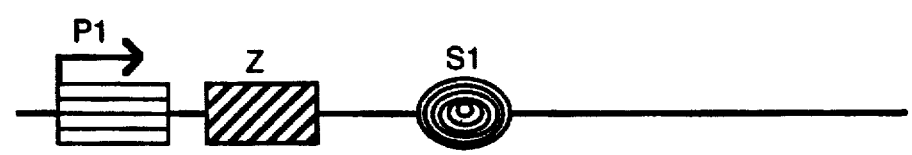
FIG. 3C is a schematic showing the basic components of a targeting construct consisting of a promoter ($P_1$), DNA sequences positioned 3' of the promoter and 5' of the switch region (Z), and switch region ($S_1$).
Figure 3D:
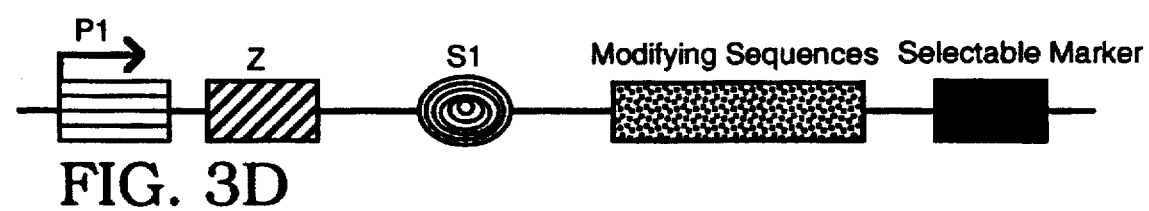
FIG. 3D is a schematic showing the basic components of a targeting construct consisting of a promoter ($P_1$), DNA sequences positioned 3' of the promoter and 5' of the switch region (Z), switch region ($S_1$), and modifying sequences, which may include additional components such as a selectable marker gene and/or an amplification gene.

The basic components of an exemplary targeting construct for use in the invention are illustrated in FIGS. 3A–3D. The minimal components of the targeting construct are (from 5' to 3'): 1) a promoter ($P_1$, where the arrow indicates the direction of transcription) and 2) a switch region (S) (FIG. 3A). The targeting construct can additionally contain 3) a modifying sequence 3' to S (FIG. 3B), and/or 4) one or more DNA sequences 5' to S (FIG. 3C). Additionally, the targeting construct can include a selectable marker (FIG. 3D). The targeting construct components are positioned so that the promoter activates transcription of the switch regions and modifying sequence. The targeting construct is normally a recombinantly or synthetically produced nucleic acid sequences, and can be used in the method of the invention as either an extrachromosomal element (e.g., a plasmid or vector) or as a stable chromosomal integrant. Exemplary modifying sequences include the $C_H$ gene for use in isotype switching (i.e., replacement of the $C_H$ gene of the target locus with a $C_H$ gene of a different isotype or subtype).

The precise mechanism through which intrachromosomal S-mediated recombination (also termed S—S recombination) occurs in the class-switch phenomenon is not fully understood (for a review on this topic, see Coffman et al., 1993, Adv. Immunol. 54:229–71). Without being held to a specific theory, naturally-occurring S-mediated recombination is triggered by simultaneous transcription of two intrachromosomal switch regions (Xu & Stavnezer (1990) Develop. Immunol. 1:11–17; Rothman et al. (1990) Mol. Cell Biol. 10:1672–1679; Jung et al. (1993) Science 159:984–987). For example, in a cell producing IgM antibody, the IgM heavy chain gene (which includes a $V_H D_H J_H$ region, a switch region (Sμ), and a Cμ gene) is constitutively transcribed and translated. Class-switching (e.g., to production of IgG) occurs when a second switch region (e.g., Sγ) is transcribed. Transcription of a second switch region is thought to be regulated by control elements associated with each of the switch regions of the $C_H$ locus. Each of these control elements are activated by a different combination of cellular signals (i.e., one or more cellular signals) normally associated with cytokines which can be activated, for example, in a microbial infection or inflammation (e.g., cytokines such as interleukins, interferons, and tumor necrosis factor). In turn, production of cellular signals is associated with specific types of infections and inflammation. Thus, a specific type of infection or inflammation results in: 1) production of a specific combination of cellular signals, which in turn determines 2) which of the switch region control elements is activated and, as a result, 3) which switch region is transcribed to promote recombination of its associated $C_H$ region with the constitutively transcribed Sμ and Cμ regions to produce a different, specific antibody isotype (Coffman et al., 1993, supra).

Figure 4A:
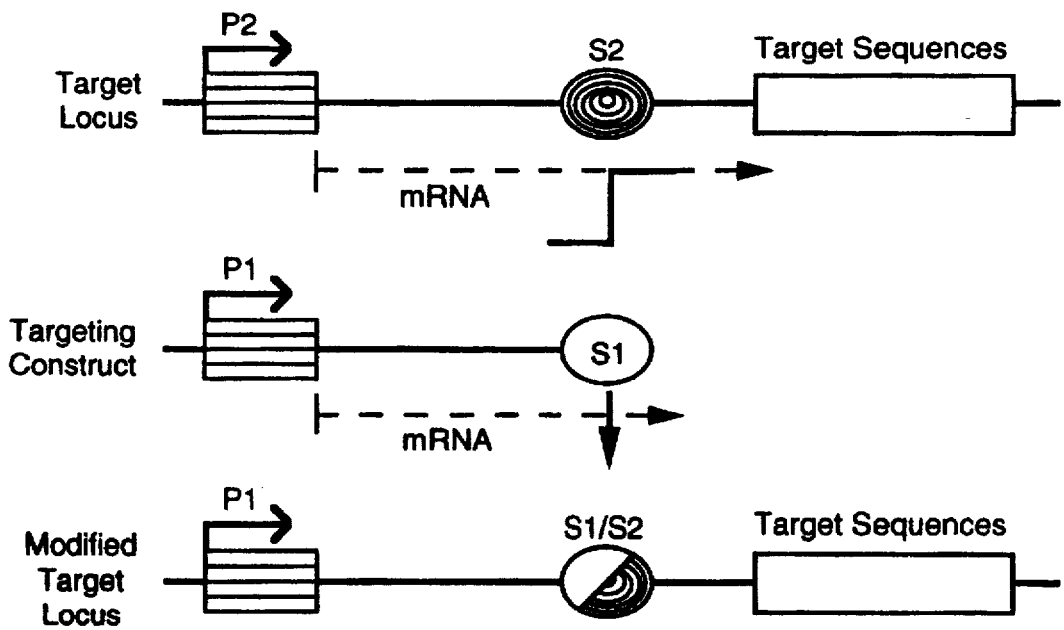
FIG. 4A is a schematic illustrating switch-mediated recombination between targeting construct $P_1$-$S_1$ and target locus $P_2$-$S_2$-T.
Figure 4B:
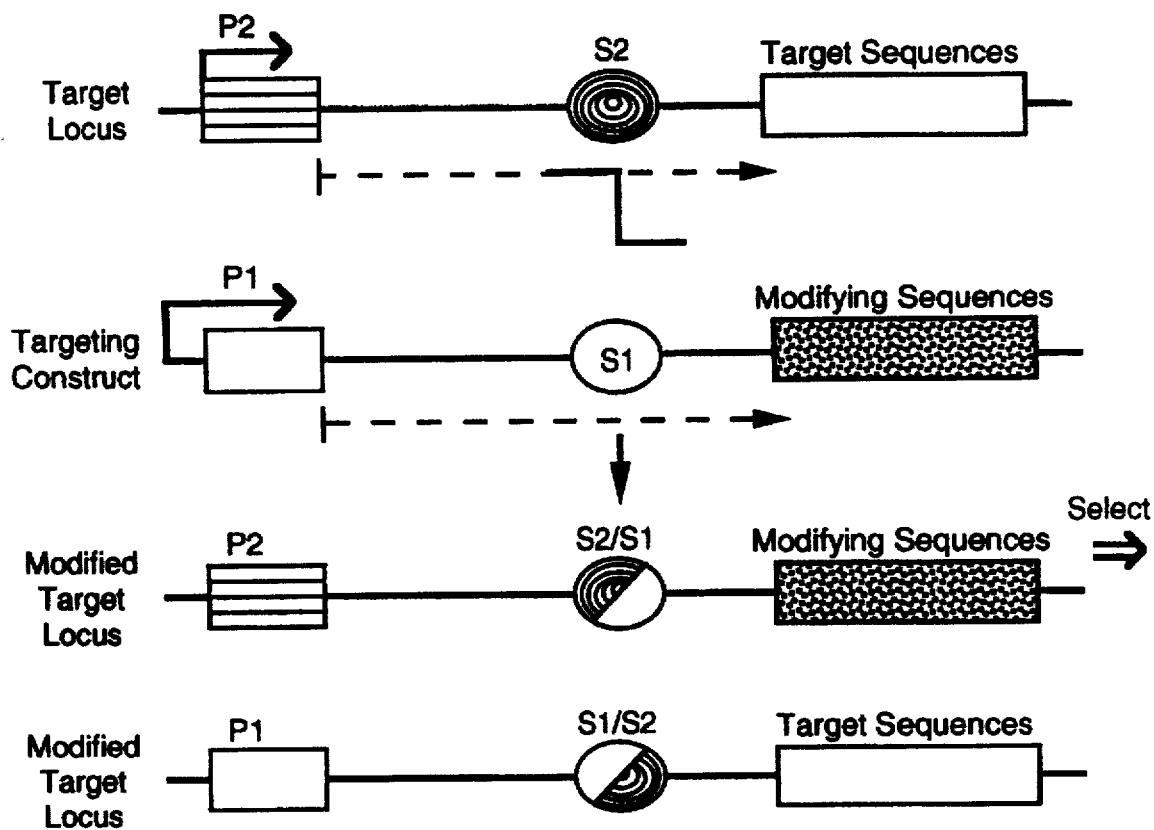
FIG. 4B is a schematic illustrating switch-mediated recombination between targeting construct $P_1$-$S_1$-M and target locus $P_2$-$S_2$-T.
Figure 4C:
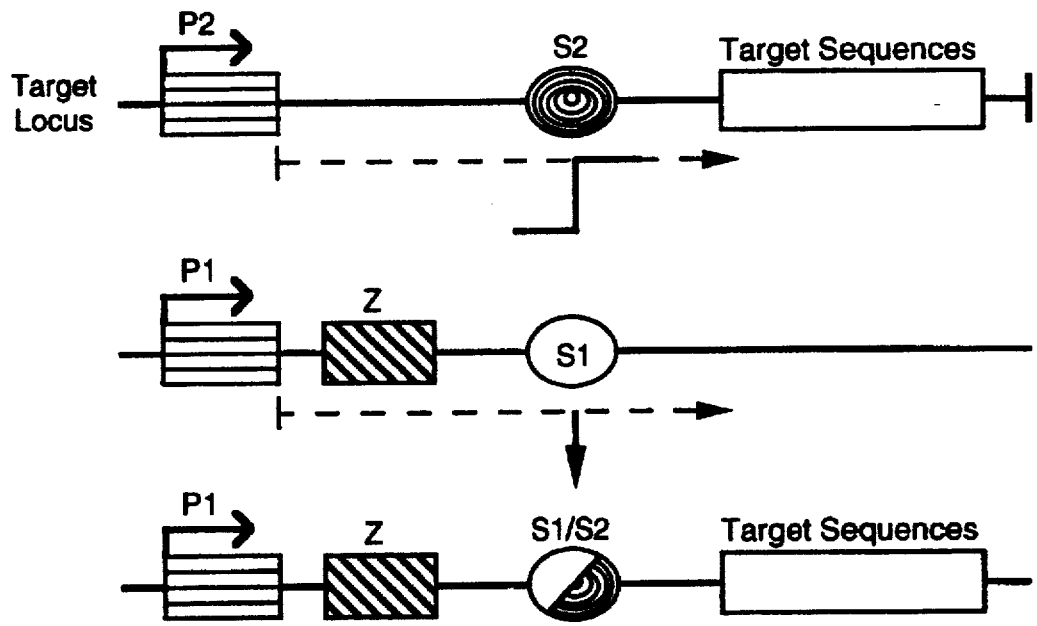
FIG. 4C is a schematic illustrating switch-mediated recombination between targeting construct $P_1$-Z-$S_1$ and target locus $P_2$-$S_2$-T.

The present invention uses switch regions to provide a method of directing recombination to pre-selected sites of interest in a manner that is not controlled by the normal cellular regulatory mechanisms described above. As illustrated in FIGS. 4A–4C, the directed S—S recombination of the present invention uses a targeting construct minimally containing a switch region ($S_1$) and a promoter ($P_1$), and a target locus containing a switch region ($S_2$) and target sequence (T) under control of a promoter ($P_2$), to facilitate switch-site specific recombination mediated by the two transcriptionally activated switch regions. The resulting recombinatorial product will minimally contain a switch region having sequences from one or both switch regions, e.g., $S_1$, or $S_1/S_2$. When the targeting construct contains a promoter $P_1$ and $S_1$, the desired recombinatorial product will consist of the $P_1$ promoter, the switch region, and the target sequence, now under control of $P_1$ instead of $P_2$ (FIG. 4A). The desired recombinatorial product is recognized in a number of ways known to the art including PCR. When $P_1$ is an inducible promoter, a cell containing the desired recombinatorial product can be recognized by induction of transcription. When the targeting construct consists of $P_1$, $S_1$, and a modifying sequence, the desired recombinatorial product will consist of the $P_2$ promoter, the switch region, and the modifying sequence which replaces the target sequence (FIG. 4B). The switch region may contain sequences from one or both switch regions, e.g., $S_1$ or $S_1/S_2$. When the modifying sequence encodes a protein or peptide, the desired recombinatorial product can be recognized by synthesis of the desired product. When the targeting construct consists of $P_1$, DNA sequences 5' to $S_1$, and $S_1$, the desired recombinatorial product contains $P_1$ and the DNA sequences 5' to the $S_1$ region inserted into the target locus (FIG. 4C). The desired recombinatorial product can be identified in a variety of ways, including PCR detection of the presence of the 5' DNA sequences and/or $P_1$, or by immunodetection technologies.

Additionally, the targeting construct can be used to insert a piece of DNA 3' to a target locus contained in a specific chromosome. In this embodiment, the targeting construct carries homologous sequences allowing insertion into the selected chromosome by homologous recombination. The resulting modified chromosome contains a DNA of the targeting construct at a site 3' from the target locus. This embodiment is useful for induction of intrachromosomal S-mediated recombination.

Switch Regions

Class-switching (or isotype switching) results when B lymphocytes initially expressing IgM switch their heavy chain isotype to IgG, IgA, or IgE upon maturation. Isotype switching results from a deletional DNA recombination event in which the $C_\mu$ constant region of the heavy chain, initially located downstream of the $V_H D_H J_H$ region, is replaced by a $C_\gamma$, $C_\alpha$, or $C_\epsilon$ constant regions (Rabbitts et al. (1980) Nature 283:351; Davis et al. (1980) supra; Kataoka et al. (1981) supra.

Several switch regions have been characterized, including the murine Sµ, Sε, Sα, Sγ$_3$, Sγ$_1$, Sγ$_{2b}$, and Sγ$_{2a}$ switch regions and the human Sµ switch region, such as Sµ, and $S_{\gamma 4}$ (Mills et al. (1995) J. Immunol. 155:3021–3036, herein specifically incorporated by reference). The murine Sµ region is about 3 kb and can be divided into a 3' region with sequences of [(GAGCT)nGGGGT]m, where n=1–7 and m=150 (Nikaido et al. (1981) supra), and a 5' region in which these two pentamers are interspersed with the pentamer sequence (C/T)AGGTTG (Marcu et al. (1982) supra). The human Sµ locus is slightly different in that the heptamer sequence is distributed throughout the region (Takahashi et al. (1982) supra; Mills et al. (1990) supra). Although other switch regions contain more complex patterns of repeated sequence, all switch sequences contain multiple copies of the pentameric sequences GAGCT and GGGGT (Nikaido et al. (1982) supra; Stanton et al. (1982) supra). The pentamers ACCAG, GCAGCC, and TGAGC are also commonly found in switch regions (Gritzmacher (1989) supra). In addition, the heptameric repeat (C/T)AGGTTG is abundantly present in switch region sequences and is found near many, but not all, switch recombination sites that have been characterized in plasmacytomas and hybridomas (Marcu et al. (1982) supra).

The murine Sε and Sα loci contain 40 bp and 80 bp sequences, respectively, that are tandemly repeated. These sequences are homologous to Sµ, especially in areas of the repeats containing the GAGCT pentamer. Both human and murine Sγ regions are much less homologous to Sγ than are the Sε and Sα regions. The homology of murine Sγ regions to Sµ decreases with the increasing distance 3' of the variable region (Sγ3>Sγ1>Sγ2>Sγ2a). The murine Sγ regions are composed of tandem repeats of 49 bp or 52 bp (Sγ2a), within which the pentameric sequences TGGGG, GCAGCC, and ACCAG are commonly found (Kataoka et al. (1981) supra; Mowatt et al. (1986) supra; Nikaido et al. (1982) supra, Nikaido et al. (1981) supra; Stanton et al (1982) supra; Szurek et al. (1985) supra; Wu et al. (1984) supra).

Switch regions suitable for use in the invention can be naturally occurring sequences, e.g., a switch region cloned directly from an Ig locus, preferably from a murine or human Ig locus. Alternatively, the switch region can be a synthetically or recombinantly produced sequence. Recombinant switch regions can have the same sequence as a native, naturally-occurring switch region, or can be modified (e.g., contain nucleotide substitutions, additions, mutations, and/or other modifications) relative to a native switch region, with the proviso that the switch region retains its function in facilitating recombination. Recombinant switch regions can be designed to as to have a minimal nucleotide sequence necessary for switch-mediated recombination at the same (or lower but acceptable) level as a native switch region, or at a level enhanced relative to recombination promoted by a wild-type switch region.

The switch-mediated recombination of the present invention provides improved efficiency of S—S recombination over the naturally-occurring mechanism, as well as providing a widely application method of producing a desired protein. This is achieved, in part, with the use of promoters providing constitutive or inducible transcription of the targeting construct, the target locus, or both the targeting construct and target locus. The improved efficiency of the switch-mediated recombination method of the invention provides a frequency of recombination at a level higher than that which occurs naturally, that is, a 1% to 100% improved efficiency; more preferably, a 20% to 100% improvement; and more preferably a 50% to 100% improvement.

Targeting Constructs

As discussed above, targeting constructs of the invention are minimally composed of: 1) a switch region and 2) a promoter operably linked to and 5' of the switch region. Additional optional components of the targeting construct include 3) a modifying sequence operably linked to and 3' of the switch region, including proteins, selectable markers, and/or control elements, and/or 4) DNA sequences 3' to the promoter and 5' to the switch region. Transcriptional activation of the promoter results in production of one or more translatable mRNA(s).

The Targeting Construct Promoter

The promoter of the targeting construct is selected according to the cell type in which directed S—S recombination is to be accomplished (e.g., a eukaryotic or prokaryotic cell, normally a eukaryotic cell). Because directed S—S recombination is dependent on transcription of the switch regions of the targeting construct and the target locus, the promoter of the targeting construct can be a constitutive or an inducible promoter. Suitable constitutive and strong constitutive promoters for DNA expression in prokaryotic or eukaryotic cells are well known in the art. Where the cell in which directed S—S recombination is to take place is a eukaryotic cell, the promoter can be the heavy chain Ig promoter or a viral promoter, such as a CMV, SV40, murine Moloney Sarcoma virus (MMLV), and spleen-focus forming virus (SFFV) promoter, or an inducible promoter, such as MMTV and α-inhibin.

The Modifying Sequence

The modifying sequence can be any nucleic acid sequence that is suitable for replacing a target sequence in a target locus. For example, the modifying sequence can be composed of a nucleotide sequence that encodes a translation product to replace all or a portion of the target sequence. For example, where the target sequence is a $C_H$ gene, the modifying sequence can be a different native $C_H$ gene, a modified $C_H$ gene (e.g, encoding an altered effector function relative to the wild-type $C_H$ gene), or a native or modified light chain constant region. Alternatively, the modifying sequence can encode a non-antibody-derived polypeptide that confers a function upon the polypeptide encoded by the modified target sequence. For example, the modifying sequence can encode a toxin, hormone, growth factor, or portions thereof. The modifying sequence can also encode a linker to provide covalent or non-covalent linkages between other (e.g., similarly modified) heavy chain gene products or non-antibody polypeptides (e.g., toxins, growth factors, hormones, or other biologically important polypeptide or other molecule). Yet another example of a modifying sequence is a nucleotide sequence encoding a detectable polypeptide label or tag, e.g., β-galactosidase, alkaline phosphatase, horseradish peroxidase, or an immunodetectable polypeptide to which an antibody can bind to facilitate polypeptide detection and/or isolation (e.g., by immunoaffinity chromatography).

Alternatively or in addition, the modifying sequence can contain regulatory sequences (e.g., a promoter, enhancer element, an intron, or a ribosome binding site) that can be used to either introduce regulatory sequences at a position 3' of a switch region, or to replace regulatory sequences already present in the target sequence. For example, switch-mediated recombination can be used to replace a weak promoter with a strong promoter in a target locus, where the weak promoter is positioned 3' or 5' of the target locus switch region. Exemplary regulatory sequences of particular interest in the modification of an Ig locus include a heavy chain enhancer sequence, a kappa chain enhancer sequence, or a promoter derived from MMLV, Rous sarcoma virus (RSV), or SFFV.

The targeting construct may also contain an amplification gene that allows the modified target locus to be amplified switch-mediated product. There are a number of suitable amplification genes known to the art and useful in the invention, for example, the gene encoding dihydrofolate reductase (DHFR).

The modifying sequence is selected according to a variety of factors including the target sequence to be modified, and/or the diagnostic or therapeutic use intended for the resultant recombinatorial product.

Additional Sequences Present 3' of the Promoter and 5' of the Switch Region

The targeting construct can contain an additional, transcribable and translatable DNA sequence operably positioned between the promoter and switch region of the target locus. This additional sequence can encode an N-terminal portion of the polypeptide encoded by the target locus. For example, the targeting construct can encode a desired $V_H D_H J_H$ polypeptide. Upon directed switch-recombination with a target locus encoding an Ig heavy chain locus having a desired $C_H$ gene at the target sequence, the recombinatorial product contains the desired $V_H D_H J_H$ region and the desired $C_H$ coding region, with the switch region positioned between.

Other Components

The targeting construct can be based upon any of a variety of vectors that are well known in the art and commercially available (e.g., pBR322, pACYC vectors, plasmids, and viral vectors). "Vectors" include any DNA or RNA molecule (self-replicating or not) that can be used to transform or transfect a desired cell. The targeting construct can include other components such as a selectable marker to facilitate screening and selection of cells containing the targeting construct as an extrachromosomal or chromosomally integrated element, and/or to select for cells that have successfully undergone directed S—S recombination, e.g., a selectable marker associated with the modifying sequence that is recombined into the target locus in addition to the modifying sequence. Suitable selectable marker genes include genes encoding a detectable marker (e.g., β-galactosidase) or drug resistance genes, e.g., hygromycin resistance (hyg), guanosine phosphoryl transferase (gpt), neomycin resistance (neo), dihydrofolate reductase (DHFR), puromycin (spt) and ampicillin resistance (Amp). The construct can also include an origin of replication for stable replication of the construct in a bacterial cell (preferably, a high copy number origin of replication), a nuclear localization signal, or other elements which facilitate production of the DNA construct, the protein encoded thereby, or both. For eukaryotic expression, the construct may also an amplification gene, which can increase levels of expression of the DNA of interest, particularly where the DNA of interest is a cDNA (e.g., contains no introns of the naturally-occurring sequence). Any of a variety of amplification genes known in the art may be used, including DHFR.

Target for Use with Targeting Constructs

As discussed above, a target locus suitable for use in the method of the invention is minimally composed of: 1) a switch region, 2) a target DNA sequence adjacent and 3' of the switch region, and 3) a promoter operably positioned in the construct to provide transcription of the switch region and target sequence as an mRNA molecule. The target locus can further contain an additional DNA sequence positioned adjacent and 5' of the switch region; in such constructs, the promoter provides transcription of the additional DNA sequence, the switch region, and the target sequence as a one or more translatable mRNA(s).

In general, target loci suitable for use with the targeting constructs of the invention can be any switch-containing sequence in which the switch region is transcribed and can facilitate switch-mediated recombination. The target locus can be any native, endogenous chromosomal sequence which contains a switch region (e.g., an Ig heavy chain locus). Alternatively, the target locus can be an artificially, recombinantly produced sequence present as either an extrachromosomal element (e.g., a vector or plasmid) or a chromosomally integrated element. In a specific embodiment of the invention, where it is desirable to insert a portion of a targeting construct 3' of a target locus on the same chromosome, the targeting construct carries homologous sequences directing recombination at a site 3' of a target locus. S-mediated recombination will then take place intrachromosomally, thus allowing controlled induction of intrachromosomal recombination.

The Promoter

The promoter of the target locus ($P_2$) can be the promoter that is present in the native, naturally-occurring target locus sequence and/or the target sequence, or a promoter that is heterologous to the target locus sequence and/or the target sequence. Because S—S recombination is associated with transcription of the switch region, the target locus promoter preferably provides at least low-level expression, more preferably constitutive expression, and even more preferably, provides high levels of constitutive expression of the target locus, specifically of the switch region-encoding DNA. Where the promoter associated with the target locus provides inadequate levels or undesirably low levels of transcription of the switch region, the native target locus promoter can b & modified or replaced with a different promoter using S-mediated recombination or other recombinant methods well known in the art, e.g., cloning, homologous recombination).

Additional Sequences Present 3' of the Promoter and 5' of the Switch Region

As discussed above, the target locus can contain an additional, transcribable and translatable DNA sequence operably positioned between the promoter and switch region of the target locus. For example, the additional sequences may encode an N-terminal portion of the polypeptide and the target locus contains a target sequence encoding the C-terminal portion of a polypeptide. After directed switch-mediated recombination, the modified target locus will contain both the N- and C-terminal portions of the polypeptide.

Other Components

The target locus can include additional components to facilitate replication in prokaryotic and/or eukaryotic cells, integration of the construct into a eukaryotic chromosome, and markers to aid in selection of and/or screening for cells containing the construct (e.g., the detectable markers and drug resistance genes discussed above for the targeting construct). For eukaryotic expression, the construct should preferably additionally contain a polyadenylation sequence positioned 3' of the gene to be expressed. The polyadenylation signal sequence may be selected from any of a variety of polyadenylation signal sequences known in the art. Preferably, the polyadenylation signal sequence is the SV40 early polyadenylation signal sequence. Expression of the target locus can also be enhanced by inclusion of intronic sequences, as discussed above for the targeting construct.

An exemplary recombinant target locus of the invention is composed of (from 5' to 3): 1) a promoter, 2) a first multiple cloning site for insertion of a DNA sequence 5' to the switch region, 3) a switch region, and 4) a second multiple cloning site for insertion of a target DNA sequence. For example, where the target locus is a recombinant Ig heavy chain gene, a $V_H D_H J_H$ DNA sequence is inserted 5' to the switch region at the first multiple cloning site, and the target sequence is a $C_H$ region inserted into the second cloning site.

Cell Lines Suitable for Use with the Method of the Invention

Any mammalian cell line capable of expressing the target locus of interest is suitable for use in the present invention. For example, where the target locus is an Ig heavy chain gene, the cell line is any mammalian cell capable of expressing a functional antibody. Of particular interest is the use of the switch-mediated recombination method of the invention to facilitate class-switching in antibody-producing cells or cells with antibody-producing potential (e.g., stem cells). For example, the cell line can be, e.g., a hybridoma cell line expressing human antibodies, an embryonic stem cell (e.g., a murine embryonic stem cell), a hybridoma cell line produced from B cells from a transgenic animal (e.g., a transgenic mouse), or any other cell (normally a mammalian cell) capable of expressing at least a functional portion of a heavy chain Ig locus or at least a functional portion of a light chain Ig locus. One example of a cell line useful in the method of the invention is a hybridoma cell line expressing human antibodies derived from B cells from the Xenomouse (Green et al. (1994) Nature Genetics 7:13 and PCT patent publication No. WO 94/02602, both of which are herein specifically incorporated by reference). The Xenomouse carries large segments of the human heavy chain and K chain loci integrated into its germline, as well as containing functionally inactivated mouse heavy and kappa light chain alleles. Xenomouse produces B cells expressing human heavy chain (hμ) and human K light chain (mK), or hμ and mouse lambda (mλ) light chain. Co-expression of hκ and mλ does not occur, since expression of one light chain completely excludes the expression of the other (Green et al. (1994) supra). Upon immunization, Xenomouse produces a broad adult-like repertoire of human Ig and give rise to antigen-specific human monoclonal antibodies. Xenomouse allows generation of mouse hybridomas making antigen-specific human monoclonal antibodies. Methods for producing hybridoma cell lines are well known in the art (see, for example, Harlow and Lane, eds., 1988, *Antibodies: A Laboratory Manual*, Cold Spring Harbor Laboratory, Cold Spring Harbor, N.Y.). Methods for producing cell lines expressing human or "humanized" antibodies are also well known in the art (see, for example, PCT Publication Nos. WO 94/02602 and WO 91/10741).

Where the cell line is an antibody-producing lymphoid cell line, the cell line can express the antibody from either a genomic sequence, a modified sequence, a heterologous sequence (e.g., an Ig sequence from another species), a modified heterologous sequence, or a chimeric sequence (e.g., composed of both murine and human Ig sequences). Thus, the cell line can be, for example, a murine hybridoma cell line producing either a murine, human, or chimeric antibody. The hybridoma cell line can be producing human antibodies by, for example, expression of human Ig genes. In one embodiment, the cell is a murine lymphoid cell producing a human antibody by expression of human Ig genes. In one variation of the embodiment, the constant region gene of the genomic sequence is a human constant ($hC_H$) region gene, e.g., a $hC_H$ gene of the mu class ($hC_H\mu$), and the modifying sequence is a human constant region of the gamma class ($hC_H\gamma$).

Methods Using Switch-Mediated Recombination

Switch-mediated recombination using the construct(s) of the invention can be accomplished in a variety of ways. For example, 1) the target locus can be naturally occurring (chromosomally located) and the targeting construct can be used as either an extrachromosomal or chromosomally integrated element; or 2) the target locus can be a naturally occurring or recombinantly produced sequence that is either present as an extrachromosomal or a chromosomally integrated element, and the targeting construct can be used as either an extrachromosomal or chromosomally integrated element. When the targeting construct and target locus are both chromosomally integrated, they are integrated on the same or different chromosomes.

Switch-Mediated Recombination Using a Chromosomal Target Locus and a Chromosomally Integrated Targeting Construct In this embodiment, the cell line used to accomplish directed switch-mediated recombination either: 1) contains an endogenous, naturally occurring target locus, or 2) contains a chromosomally integrated recombinant target locus. Methods for introduction of DNA into a host cell and selection for stable chromosomal integrants containing a specific DNA sequence of interest are well known in the art (see, for example, Sambrook, et al., 1989, *Molecular Cloning: A Laboratory Manual*, 2nd Ed., Cold Spring Harbor Laboratory Press, Cold Spring Harbor, N.Y.; hereby incorporated by reference with respect to methods and compositions for recombinant DNA techniques to provide a transformed cell containing a stably integrated DNA of interest, and expression of the DNA of interest).

The targeting construct can be linearized, e.g., by digestion with a restriction endonuclease(s), and the linear DNA introduced into the host cell using any of a variety of methods known in the art (e.g., electroporation, microinjection, liposome fusion, red blood cell ghost fusions, protoplast fusion, yeast cell fusion, or any other method known in the art (see, for example, Sambrook et al., supra)). The linear vector is then integrated into the cell's genome randomly or specifically by directed homologous recombination, and stable integrants are selected by, for example, expression of a selectable marker associated with the targeting construct, or by expression of the modifying sequence in the targeting construct.

Directed switch-mediated recombination is accomplished by simultaneous transcription of the switch regions in the target locus and the targeting vector. Cells containing the recombinatorial product, for example, the modified target locus, are identified and selected by expression of the modified target locus gene product (e.g., by ELISA reactivity or fluorescence-activated cell sorting (FACS)).

Switch-Mediated Recombination Using a Chromosomal Target Locus and an Extrachromosal Targeting Construct In this embodiment of the method of the invention, the targeting construct is introduced-into the cell containing a chromosomally integrated target locus by methods well known in the art (see, for example, Sambrook et al., 1989, supra). In contrast to the method immediately above, the targeting construct is maintained as an extrachromosomal element for a time sufficient for transcription of the targeting construct's switch region and recombination with the transcriptionally active switch region of the target locus. Cells containing the desired recombinatorial product, e.g., a modified target locus, can be identified and selected as described above, e.g., selection for expression of a selectable marker associated with the integrated target sequence, or detection of cells expressing the desired modified target locus gene product.

Screening and Selection

Detection of properly recombined sequences can be accomplished in a variety of ways, depending upon the nature of the desired recombinatorial product. For example, where the modifying sequence associated with a selectable marker is recombined into the target locus with the modifying sequence, an initial screen will select for those cells which express the marker. A second screen can be used to determine if the drug resistant cells express the appropriately modified target locus.

The method used for the second screen will vary with the nature of the modifying sequence inserted into the target locus. The modifying sequence can be detected by Southern blot using a portion of the modifying sequence as a probe, or by polymerase chain reaction (PCR) using amplifying primers derived from the modifying and modified regions. The cells having an appropriately integrated modifying sequence can also be identified by detecting expression of a functional modified target locus product, e.g., immunodetection of the new $C_H$ region in a modified antibody heavy chain locus. Alternatively, the expression product of the modified target locus can be detected using a bioassay to test for a particular effector function conferred by the modifying sequence. For example, the expression of modifying sequence that encodes a biologically active molecule such as an enzyme, toxin, growth factor, or other peptides is assayed for that particularly biological activity.

Where the target locus is an Ig gene, the product of the modified target locus can also be tested for appropriate antigen or ligand recognition via any conventional immunological screening methods known in the art, e.g, ELISA, FACS, antibody-dependent cell cytotoxicity assays, or immunoprecipitation assays (see, for example, Harlow and Lane, supra).

EXAMPLES

The following examples are put forth so as to provide those of ordinary skill in the art with a complete disclosure and description of how to make and use various constructs and perform the various methods of the present invention and are not intended to limit the scope of what the inventors regard as their invention. Unless indicated otherwise, parts are parts by weight, temperature is in degrees centigrade, and pressure is at or near atmospheric pressure. Efforts have been made to ensure accuracy with respect to numbers used, (e.g., length of DNA sequences, molecular weights, amounts, particular components, etc.) but some deviations should be accounted for.

Example 1

Targeting Construct for Switch-Mediate a Recombination (DTSW-1.4 and p TSW-1.9)

All the vectors generated were based on a low copynumber pACYC177 Plasmid (NEB). The vector pTSW-1.4 was generated from the p1bYACδNot plasmid containing a 23 kb EcoRI genomic fragment of the entire human γ2 switch region, isolated from human placenta genomic library. This fragment contained 2 kb of coding sequences, 12 kb of upstream sequences including the I exon and γ2 switch region, and 9 kb of downstream sequences (Flanagan & Rabbitts (1982) Nature 300:709–713). This plasmid also contains the mouse 3' enhancer (Dariavach et al. (1991) Eur. J. Immunol. 21:1499–1504). The vector was modified to contain a hygromycin selectable marker and a human CMV promoter-enhancer cassette, which included at its 3' end prokaryotic terminator sequences (described below). The prokaryotic terminator sequences were used to stop fortuitous prokaryotic transcripts from activating the switch sequences, and thus destabilizing them during cloning in bacteria (Mowatt & Dunnick (1986) J. Immunology 136:2674–2683). These sequences were confirmed to have very little effect on eukaryotic transcription.

The hygromycin gene, driven by the SV40 promoter (Giordano & McAllister (1990) Gene 88:285–288) was cloned as a 1.7 kb NindIII-BamHI fragment from pUC219, TG76 plasmid and inserted into NindIII and BamHI sites in pACYC177 to generate pACYC.hyg plasmid.

The terminator was synthesized as GCATGCCCGCGG-GAATAGGCGGGCTTTTTTNNNGCCGCGGCTCGA (SEQ ID NO:1), with flanking SphI sites, and an internal XhoI site at the 3' end, for cloning purposes. This sequence was cloned into the SphI site of pIK1.1Cat plasmid, downstream of the human CMV promoter-enhancer sequences.

The CMV expression cassette, together with the terminator sequences, was cloned as a 900 bp HindIII-XhoI fragment, which was placed into the HindIII and XhoI sites in the pACYC.hyg plasmid described above to generate pACYC.hyg.CMVt, in which the CMV transcription orientation is opposite to that of the hygromycin gene.

The 2.6 kb fragment, containing both hygromycin and CMV-terminator cassettes, was excised from pACYC.hyg.CMVt by BamHI and XhoI digestion. Both ends of this fragment were converted into NotI sites, using linkers, and the fragment was cloned into the unique NotI site in p1bYACδNot plasmid containing 23 kb human γ2 sequences and mouse 3' enhancer. pTSW-1.4 plasmid (FIG. 5) was generated with CMV transcription orientation in the same direction as that of the human γ2 coding sequences. pTSW-1.9 plasmid (FIG. 6) was generated with CMV transcription orientation opposite to that of the human γ2 coding sequences.

Figure 5:
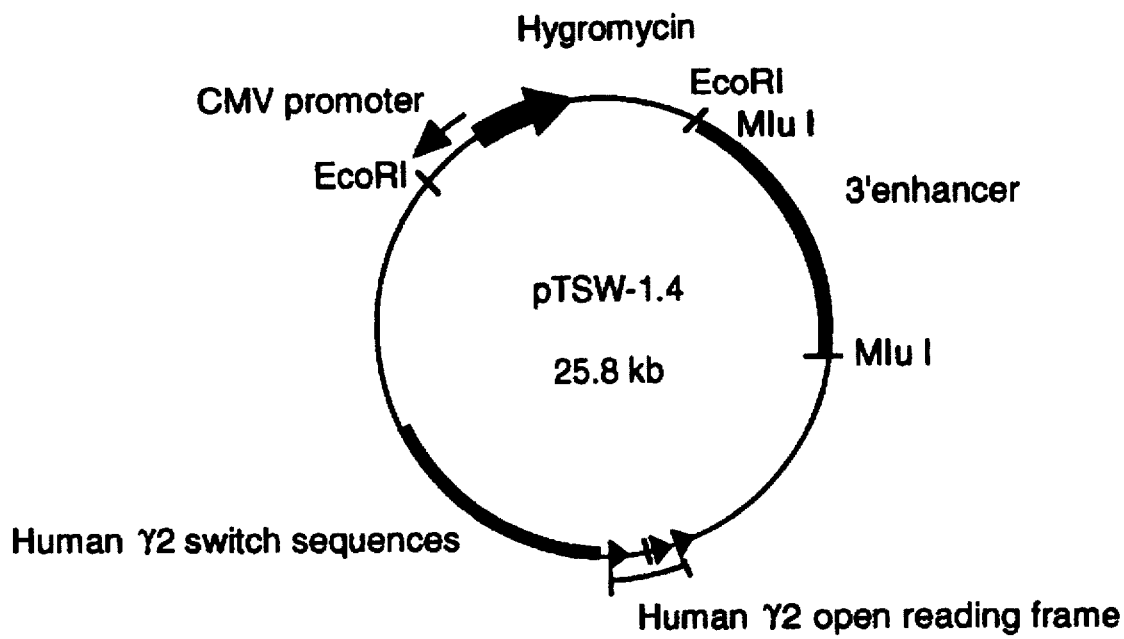
FIG. 5 is a schematic of a directed targeting construct of the invention (pTSW-1.4) having the entire 23 kb human γ2 locus (5' control elements, I exon, switch regions, coding sequences, membrane and secretory exons, polyA), mouse 3' enhancer sequence, CMV promoter/enhancer cassette, and SV2 hygromycin selectable marker.
Figure 6:
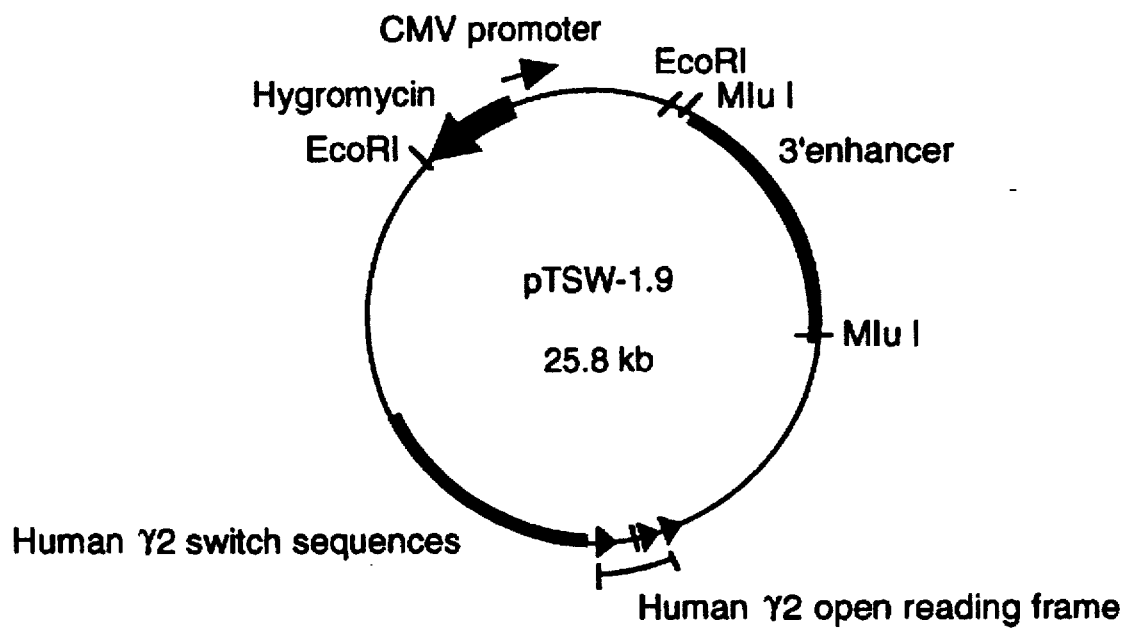
FIG. 6 is a schematic of a targeting construct of the invention (pTSW-1.9) with the elements as described in the legend to FIG. 5, with the CMV promoter/enhancer cassette in the opposite orientation to that of pTSW-1.4.

An exemplary targeting construct of the invention, designated pTSW-1.4, is shown in FIG. 5. pTSW-1.4 is constructed for use in switch-mediated replacement of an Ig heavy chain constant gene with a human heavy chain IgG$_2$ constant gene (hCHγ2). The pTSW-1.4 construct contains a CMV promoter operably linked to, in the 5' to 3' orientation, the human IgG2 heavy chain region (approximately 23 kb), which includes the IgG2 heavy chain I exon and its 5' flanking sequences, the human IgG2 switch region, the complete human hCHγ2 gene, and sequences flanking the IgG2 heavy chain region. The hCHγ2 region is linked to a murine enhancer positioned adjacent and 3' of the hCHγ2 gene. The CMV promoter is a strong constitutive promoter. Other constitutive promoters can be used instead of the CMV promoter (e.g., SSFV, MMLV, MCV, RSV, SV40, etc.). Both the hCHγ2 regions have been cloned and sequenced (Mills et al. (1995) supra). Murine 3' enhancer is also well known in the art (Dariavach et al. (1991) supra).

Example 2

Targeting a construct for switch-mediated recombination (pTSW-2)

To generate pTSW-2 plasmid, a 13 kb BamHI fragment was cloned from the 23 kb EcoRI human γ2 genomic fragment in p1byACδNot plasmid, as described in Example 1, followed by partial fill-in reaction with Klenow to generate fragment ends compatible with XhoI. This clone was inserted into the unique XhoI site in pACYCHhyg. CMVt plasmid, which was also partially filled in with Klenow to make the site compatible with Bam HI. The correct orientation of the clone, in which the transcription orientation of human γ2 coding sequences is the same as the CMVpromoter, was selected.

Figure 7:
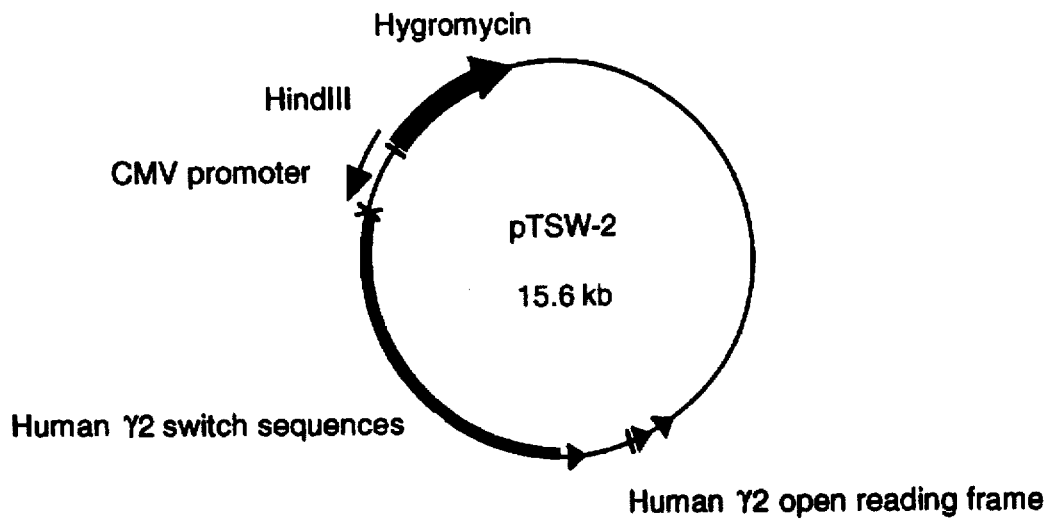
FIG. 7 is a schematic of a targeting construct of the invention (pTSW-2) having a 12 kb BamHI fragment cloned from the 23 kb human γ germline clone (including switch regions and the human γ open reading frame; the I exon and 5' control elements are not included), CMV promoter/enhancer cassette providing splice donor site, and SV2 hygromycin selectable marker; the mouse 3' enhancer is not included.

Another exemplary targeting construct of the invention, designated pTSW-2, is shown in FIG. 7. Like pTSW-1.4, pTSW-2 is constructed for use in switch-mediated replacement of an Ig heavy chain constant gene with a human heavy chain IgG$_2$ constant gene (hCHγ2). The pTSW-2 construct is prepared using a CMV promoter operably linked to, in the 5' to 3' orientation, the human IgG2 heavy chain region (approximately 13 kb) including the human IgG2 switch region and 200 bp 5' flanking sequences of the switch region and human γ2 open reading frame. Some of the flanking sequences present in pTSW-1.4 are not present in pTSW-2. The pTSW-2 construct also contains the selectable marker SV2 hyg and a prokaryotic transcription terminator (to stabilize the switch region). The pTSW-2 construct can be prepared either with or without a murine enhancer positioned 3' of the hC Hγ2 gene.

Example 3

Targeting construct for switch-mediated recombination (PTSW-3.1)

To generate pTSW-3.1 plasmid (FIG. 8), 2 kb of human γ2 coding sequences were cloned by PCR from p1bYACδNot as an XhoI-SalI fragment (Example 1). This fragment was cloned into the unique XhoI in pACYC.hyg.CMVt plasmid, 3' of the terminator sequences. Mouse γ1 switch sequences were excised as a 10 kb HindIII-EcoRI fragment from p-gamma-1/EH10.0 plasmid (Mowart & Dunnick (1986) supra), and the ends were converted into XhoI and SalI, respectively. The modified plasmid was cloned 5' of the human γ2 region via the unique XhoI site in pACYC.hyg.CMVt.pTSW-3.1dBglII plasmid (FIG. 9) was generated similarly to pTSW-3.1, except that a 7.9 kb BglII-EcoRI mouse γ1 switch sequences was included.

pTSW-3.2 was constructed as described for pTSW-3.1, except that the CMVpromoter-enhancer cassette was replaced by the spleen focus forming virus (SSFV) promoter.

pTSW-3 plasmids contained unique NotI and MluI sites (converted by a linker from the unique BamHI site). HindIII is used for linearization and for cloning of the 3' enhancer.

Figure 8:
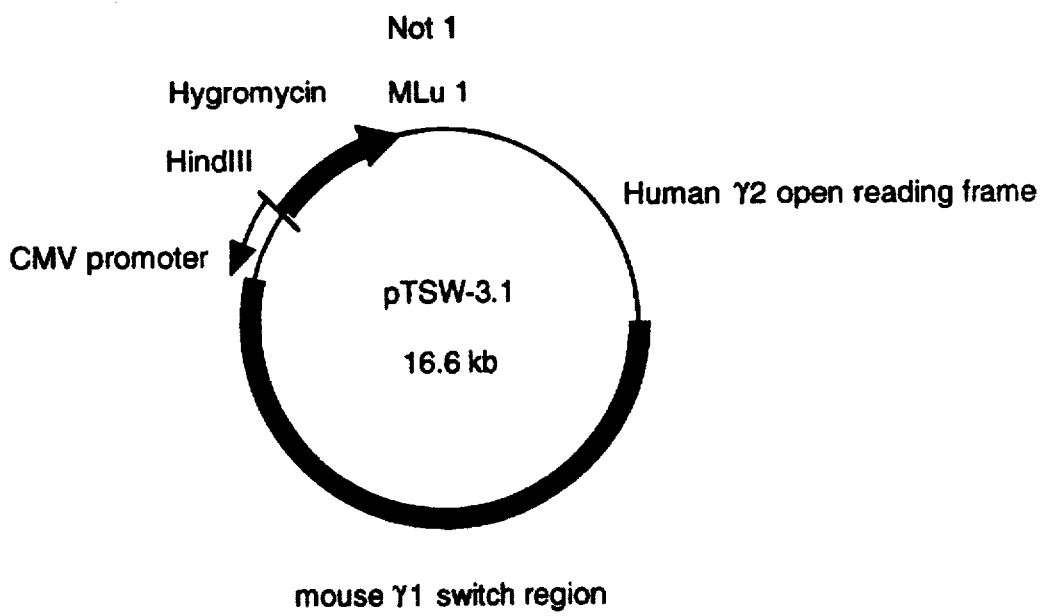
FIG. 8 is a schematic of a targeting construct of the invention (pTSW-3.1) having 10 kb of cloned HindIII-EcoRI mouse γ1 genomic switch fragment (5' control elements, I exon, and mouse γ1 switch sequences), CMV promoter cassette (SFFV promoter cassette in the pTSW-3.2 series), genomic clone of human γ2 open reading frame and splice acceptor, SV2 hygromycin selectable marker, and optionally the mouse 3' enhancer sequence.
Figure 9:
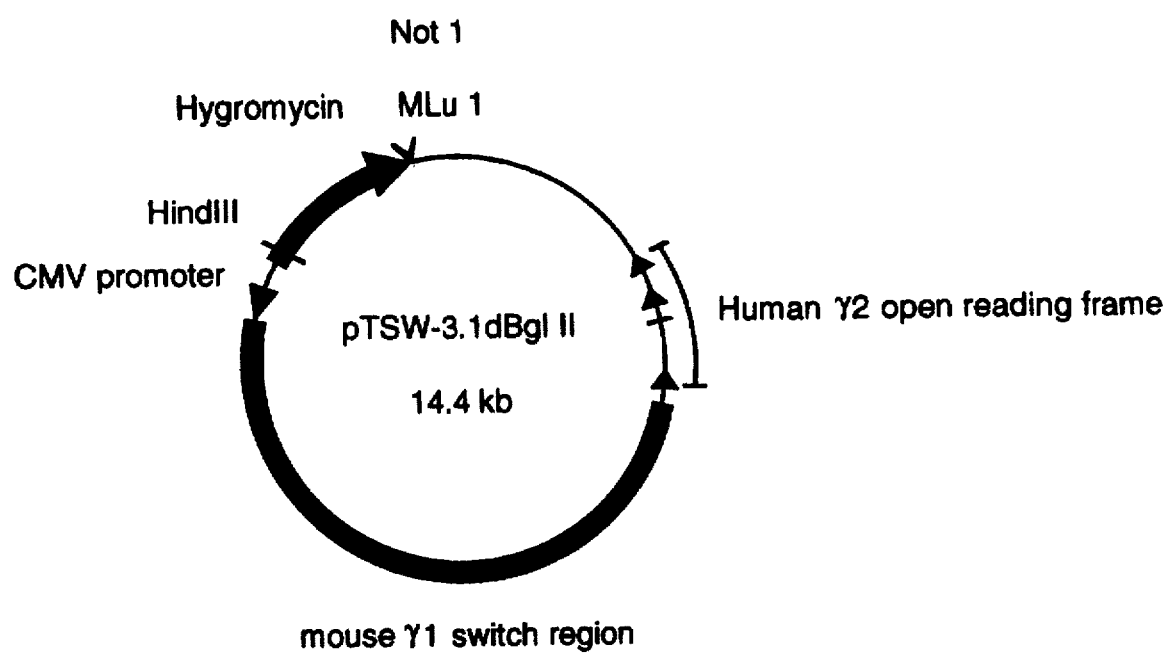
FIG. 9 is a schematic of a targeting construct of the invention (pTSW-3.1BglII) having 7.9 kb BglII-EcoRI mouse γ1 genomic switch fragment (I exon and mouse γ1 switch sequences; 5' control elements not included), CMV promoter cassette (SFFV promoter cassette in the pTSW-3.2 series), genomic clone of human γ2 open reading frame and splice acceptor, SV2 hygromycin selectable marker, and optionally the mouse 3' enhancer sequence.

A further exemplary targeting construct of the invention, designated pTSW-3.1, is shown in FIG. 8. Like pTSW-1.4 and TSW-2, pTSW-3.1 is constructed for use in switch-mediated replacement of an Ig heavy chain constant gene with a human heavy chain IgG$_2$ constant gene (hCH$_{γ2}$). The pTSW-3.1 construct is prepared using a CMV promoter operably linked to, in the 5' to 3' orientation, a murine γ1 switch region which may contain also the mouse γ1 I exon and flanking sequences, and a human genomic constant hCH$_{γ1}$, hCH$_{γ2}$, or hCH$_{γ4}$ coding sequence, which includes the 5' flanking branch point and splice acceptor. The pTSW-3.1 construct can optionally further contain a murine γ1 control element (mL$_{γ1}$) positioned adjacent and 5' of the mS$_{65}$ sequence. Alternatively, the human switch region of the γ1 gene (hS$_{γ1}$) and its 5' flanking sequences, such as the I exon (hI$_{γ1}$) can be used instead of the mL$_{γ1}$ and mS$_{γ1}$. In constructs which do not contain I exon, a splice donor site is provided 3' of the promoter sequences. The pTSW-3.1 construct may further optionally contain a murine 3' enhancer positioned adjacent and downstream of the hC$_{H\gamma}$gene and/or a 3' eukaryotic transcription terminator positioned 3' and adjacent the hC$_{H\gamma}$gene. Each of the elements of the pTSW-3 construct are well known in the art (mouse S$_{\gamma4}$, S$_{\mu}$, Mills et al. (1991) supra; mouse S$_{\gamma1}$, Mowatt & Dunnick (1986) supra; human Sγ, Mills et al. (1995) supra; mouse 3' enhancer, Dariavach et al. (1991) supra). The pTSW-3.1 construct also contains the selectable marker SV2γ2hyg and a HindIII linearization site. Other selectable markers may be used, for example, pyromycin.

Example 4

Switch-mediated recombination in a hybridoma cell line

As discussed above, one of the problems associated with production of human monoclonal antibodies is that the immortal cell line fused with the human B cells is of murine origin. This can result in a recombinatorial event where the resulting antibody has a human variable region (human light chains and human heavy chain variable region (hV$_H$D$_H$J$_H$)), but has a murine heavy chain constant region (mC$_{H\gamma}$) (see FIG. 8). Switch-mediated recombination is used to replace the mC$_{H\gamma}$gene with a human heavy chain constant region (hC$_{H\gamma}$) gene.

A hybridoma cell line expressing a monoclonal IgG antibody against antigens, including human antigens, having a human heavy chain variable region (hV$_H$D$_H$J$_H$) and a murine heavy chain constant region (mC$_{H\gamma}$) is produced using methods well known in the art (for example, see, Green et al. (1994) supra). A targeting construct containing a promoter operably linked to a switch region and the hC$_{H\gamma}$gene is constructed as described above. Any of the exemplary vectors described in the examples above (pTSW-1.4, pTSW-2, or pTSW-3.1) is suitable for use in this method. The construct is linearized, and the linear construct introduced into the hybridoma cell by, for example, electroporation, lipofection, or other methods known to the art. The transfected hybridoma cells, containing stable integrants of the construct, are selected by their ability to grown in hygromycin. Hygromycin resistant cells are then cultured further to allow for transcription of the target construct from the CMV promoter and the resulting switch-mediated recombinatorial event. Hybridoma single cell cultures are then screened for expression of hC$_{H\gamma2}$ by amplification of recombined antibody message or by using an anti-human IgG2 antibody in a sandwich ELISA assay, or isolated by FACS sorting.

Example 5

Switch-mediated recombination in a transgenic mouse producing human antibodies

Switch-mediated recombination may be accomplished in a transgenic mouse in vivo as follows. The targeting vector is introduced as a transgene into a human antibody-producing mouse and the recombined antibodies, produced by mouse B cells or their derived hybridomas, are screened as described.

The instant invention is shown and described herein in what is considered to be the most practical, and preferred embodiments. It is recognized, however, that departures may be made therefrom which are within the scope of the invention, and that modifications will occur to one skilled in the art upon reading this disclosure.

What is claimed is:

1. An artificial nucleic acid targeting construct comprising:
   a) a switch region;
   b) a promoter operably linked to and 5' of the switch region; and
   c) a modifying sequence operably linked to and 3' of the switch region.

2. The targeting construct of claim 1, further comprising an additional DNA sequence, said additional DNA sequence positioned 5' of the switch region and 3' of the promoter.

3. The targeting construct of claim 1, wherein the modifying sequence encodes a constant region of an antibody heavy chain.

4. The targeting construct of claim 1, wherein the modifying sequence encodes an immunoglobulin variable region, a promoter, an enzyme, a toxin, a hormone, a growth factor, a detectable peptide label, or a linker polypeptide.

5. The targeting construct of claim 1, wherein the promoter is a constitutive or inducible promoter.

6. An isolated cell selected form the group consisting of a B cell and a B cell hybridoma, the cell comprising the targeting construct of claim 1.

7. The targeting construct of claim 3, wherein the constant region is the constant region of a human antibody heavy chain.

8. The targeting construct of claim 3, wherein the modifying, sequence encodes a constant region of a murine antibody heavy chain.

9. The targeting construct of claim 3, wherein the constant region is selected from the group consisting of Cγ, Cμ, Cα, Cδ, and Cε.

10. The targeting construct of claim 5, wherein the promoter is selected from the group consisting of a cytomegalovirus promoter, a spleen-focus forming virus (SFFV) promoter, a Rous sarcoma virus promoter, an SV40 promoter, and a murine Maloney virus promoter.

11. An isolated cell selected from the group consisting of a B cell and a B cell hybridoma, the cell comprising a genome which has been subjected to directed switch-mediated recombination via an exogenous nucleic acid targeting construct, said targeting construct comprising a switch region and a promoter operably linked to and 5' of the switch region.

12. The cell of claim 11, wherein said targeting construct further comprises a modifying sequence operably linked to and 3' of the switch region.

13. The cell of claim 12, wherein said modifying sequence encodes a constant region of an antibody heavy chain.

14. The cell of claim 13, wherein said antibody heavy chain is a human antibody heavy chain.

15. A method for performing directed switch-mediated recombination, the method comprising the steps of:
   a) introducing a targeting construct into an isolated B cell or B cell hybridoma,
   wherein the targeting construct comprises a switch region, and a promoter ($P_1$) operably linked to and 5' of the switch region, and
   wherein the cell comprises a target locus comprising a switch region, and a promoter ($P_2$) operably positioned within the target locus to provide transcription of the switch region and target sequence; and
   b) culturing the cell to allow transcription of the target locus and the targeting construct, thereby promoting recombination between the target locus switch region and the targeting construct switch region; and
   c) selecting a cell comprising a modified target locus comprising the targeting construct $P_1$, a switch region, and the targeting construct,
   wherein $P_1$, the switch region, and the target sequence are operably linked and wherein the target sequence is under the control of $P_1$, indicating that directed switch-mediated recombination has occurred.

16. A method for performing directed switch-mediated recombination, the method comprising the steps of:
   a) introducing a targeting construct into an isolated B cell or B cell hybridoma,
   wherein the targeting construct comprises a switch region, and a promoter ($P_1$) operably linked to and 5' of the switch region, and a modifying sequence operably linked to and 3' of the switch region,
   wherein the cell comprises a target locus comprising a switch region, a target sequence adjacent and 3' of the switch region, and a promoter ($P_2$) operably positioned within the target locus to provide transcription of the switch region and target sequence; and
   b) culturing the cell to allow transcription of the target locus and the targeting construct, thereby promoting recombination between the target locus switch region and the targeting construct switch region; and
   c) selecting a cell comprising a modified target locus comprising the targeting construct $P_1$, a switch region, and the modifying sequence,
   wherein $P_1$, the switch region, and the modifying sequence are operably linked, indicating that directed switch-mediated recombination has occurred.

17. The method of claim 16, wherein the target locus encodes an antibody heavy chain.

18. The method of claim 16, wherein the target locus encodes a murine antibody heavy chain and the modifying sequence of the target construct is a human antibody heavy chain constant region.

19. The method of claim 16, wherein the target locus further comprises a non-target sequence positioned between the target locus promoter and the target locus switch region.

20. The method of claim 16, wherein the targeting construct is linearized prior to step a), and a cell containing a stable integrant of the targeting construct is selected prior to step b).

21. The method of claim 16, wherein the targeting construct is extrachromosomal.

22. The method of claim 19, wherein the non-target sequence encodes a human antibody heavy chain variable region, the target sequence encodes a murine antibody heavy chain constant region, and the modifying sequence of the targeting construct encodes a human antibody heavy chain constant region.

23. A method for producing a modified antibody by switch-mediated recombination, the method comprising the steps of:
   a) introducing a targeting construct into an isolated antibody-expressing B cell or B Cell hybridoma, wherein the targeting construct comprises a switch region ($S_1$), a promoter operably linked to and 5' of the switch region, and a modifying sequence operably linked to and 3' of the switch region, and
   wherein the antibody heavy chain expressed by the cell is encoded by an antibody heavy chain locus comprising a promoter, an antibody heavy chain variable region operably linked to and 3' of the promoter, a switch region ($S_2$) adjacent and 3' of the variable region, and an antibody heavy chain constant region adjacent and 3' of the switch region,
   b) culturing the cell to allow antibody expression and transcription of the targeting construct, wherein switch-mediated recombination between said $S_1$ and $S_2$ is promoted and wherein said heavy chain locus constant region is replaced with the modifying sequence of the targeting construct;
   c) selecting a cell comprising a modified heavy chain locus comprising the heavy chain locus promoter, the heavy chain variable region, a switch region, and the modifying sequence of the targeting construct, wherein the heavy chain locus promoter, the variable region, the switch region, and the modifying sequence are operably linked,
   wherein a modified antibody is produced.

24. An isolated nucleic acid target locus comprising: a switch region, a first cloning site for insertion of a non-target sequence, the first cloning site being adjacent and 5' of the switch region, a second cloning site for inserting of a target sequence, the second cloning site being adjacent and 3' of the switch region, and a promoter operably linked to and 5' of the first cloning site, wherein transcriptional activation of the promoter provides transcription of the non-target sequence, the switch region, and the target sequence.

25. The target locus of claim 24, wherein the switch region, first cloning site, second cloning site and promoter are operatively linked in a plasmid.

* * * * *

UNITED STATES PATENT AND TRADEMARK OFFICE
Certificate

Patent No. 5,714,352                                                    Patented: February 3, 1998

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Aya Jakobobits, Menlo Park, CA; Michael Lajos Gallo, San Jose, CA; Xiao-Ping Yang, Foster City, CA.

Signed and Sealed this Ninth Day of May, 2000.

GEORGE C. ELLIOTT, PH.D.
*Supervisory Patent Examiner*
Art Unit 1636